United States Patent
Kris et al.

(10) Patent No.: US 9,824,852 B2
(45) Date of Patent: Nov. 21, 2017

(54) CD-SEM TECHNIQUE FOR WAFERS FABRICATION CONTROL

(71) Applicant: Applied Materials Israel Ltd., Rehovot (IL)

(72) Inventors: Roman Kris, Jerusalem (IL); Yakov Weinberg, Modi'in (IL); Yan Ivanchenko, Nes-Ziona (IL); Ishai Schwarzband, Or-Yehuda (IL); Dan Lange, Haifa (IL); Arbel Englander, Tel Aviv (IL); Efrat Noifeld, Rehovot (IL); Ran Goldman, Hod Hasharon (IL); Ori Shoval, Ashdod (IL)

(73) Assignee: Applied Materials Israel Ltd, Rehovot (IL)

(*) Notice: Subject to any disclaimer, the term of this patent is extended or adjusted under 35 U.S.C. 154(b) by 0 days.

(21) Appl. No.: 14/985,847

(22) Filed: Dec. 31, 2015

(65) Prior Publication Data

US 2017/0194125 A1    Jul. 6, 2017

(51) Int. Cl.
H01J 37/22    (2006.01)
H01J 37/28    (2006.01)
G01N 23/225   (2006.01)
G01B 15/04    (2006.01)

(52) U.S. Cl.
CPC ......... *H01J 37/222* (2013.01); *G01B 15/04* (2013.01); *G01N 23/2251* (2013.01); *H01J 37/28* (2013.01); *G01N 2223/07* (2013.01); *G01N 2223/102* (2013.01); *G01N 2223/401* (2013.01); *G01N 2223/418* (2013.01); *G01N 2223/6116* (2013.01); *G01N 2223/646* (2013.01); *H01J 2237/24592* (2013.01); *H01J 2237/2813* (2013.01)

(58) Field of Classification Search
USPC ....................................... 250/306, 307, 310
See application file for complete search history.

(56) References Cited

U.S. PATENT DOCUMENTS

2015/0243568 A1* 8/2015 Fischer ................ H01L 22/26
                                                    438/8

\* cited by examiner

*Primary Examiner* — Kiet T Nguyen
(74) *Attorney, Agent, or Firm* — Lowenstein Sandler LLP

(57) ABSTRACT

A Critical Dimensions Scanning Electron Microscope (CD-SEM) is described that comprises a unit for performing CD-SEM measurements of a semiconductor wafer, a BSE imaging unit for obtaining a Grey Level image (GL) of the wafer, and a unit for GL analysis and for processing the GL analysis results with reference to results of the CD-measurements.

20 Claims, 6 Drawing Sheets

CD-SEM TECHNIQUE FOR WAFERS FABRICATION CONTROL

FIELD

The present disclosure relates to a technique for controlling a process of manufacturing semiconductor wafers, based on using a Critical Dimensions Scanning Electron Microscope (CD-SEM or CDSEM).

BACKGROUND

Critical Dimension Scanning Electron Microscope (CD-SEM or CDSEM) is a traditional solution for inline fabrication process control of semiconductor wafers. The CDSEM measurements are extracted from top-down images based on secondary electron collection while scanning the specimen.

Modern CD-SEMs are known to deliver accurate measurement results of patterned wafer surfaces (post Litho, post Etch, post Polish) with high precision (typ.0.1 . . . 0.7 nm) at the highest possible SEM resolution (typ. 1.4 nm) by use of very low voltage and probe currents (typ.300V . . . 2 kV 15 . . . 50 pA) with very high throughput (time for move-acquire-measure or MAM time typ. 4 s).

Measurements taken by CD-SEM today, are based on analysis of acquired grey level images as generated by secondary electrons (SE) edge contrast mechanism. SE are characterized by their low energy <50 eV.

Secondary electrons hold majority of the detection yield. These images provide more on the topographical information of the specimen surface and less in terms of material contrast.

In some cases there is too much structural information in the image which can irritate the measurement, in other cases small but important differences between various material compounds cannot be detected, as images are limited by contrast information and resolution of primary scanning beam.

More specifically, at 28 nm technology and below, limits arise for precise metrology and especially for post etch measurements, due to introduction of new material compounds stacks and processes with variable and complex texture as well as reduced feature sizes corresponding to so-called HAR (High Aspect Ratio) structures.

At more advanced technologies beyond 28 nm, due to HAR and 3D complex structures, the bottom signal of SE is close to zero. For example, the multi-stack layer or grains which become visible in open copper area on the via bottom, as well as large process variations can irritate the measurement algorithm and lead to wrong measurement results. Edge-based measurements become insufficient for process control, where measurements based on a bottom signal are needed, since the bottom signal carries information on material and/or non-topographic properties of deep layers.

For example, Back End Of Line (BEOL) metrology, at a final measurement step post etch for the "Trench First Via Last" (TFVL) integration, had been confronted with significant reduction in the yield of SEs coming from the bottom surface edges of vias (i.e., deep channels in a wafer layer/s). At this TFVL integration, first a metal hard mask is patterned for trench forming, and after that a via is etched within the trench down to the underlying copper line. When scanning by a primary beam across the measurement structure, the hard mask is charged up positively (so more electrons escape than are injected by the primary incident beam. This positive charge attracts most of the SE escaping from the bottom of the via. Hence, the number of electrons which arrive at a detector is reduced.

In practice of the SE imaging, for more accurate inspection of wafers and for control of the process, either visual analysis by human operators or/and destructive material analysis is required.

There is an alternative technique, known as Back Scattered Electron (BSE) Imaging, for example a Low Loss BSE (LL-BSE) imaging.

The key at BSE imaging is the collection of only the back scattered electrons (BSE) from outermost specimen surface, which undergo the least amount possible of energy loss in the process of image generation following the impact of the material by a primary beam. In BSE, very good and measurable material distinction and sensitivity can be achieved even for very low density material compounds.

In order to proceed with the description, some comprehensive definitions have been introduced below, which are important for understanding the problem and the exemplary solutions which will be described below.

SEM—Scanning Electron Microscope used for exposing a semiconductor wafer to a primary electron beam, collecting data on responsive electron beams or scattering electrons from one or more layers of the wafer and further reconstructing the obtained SEM image by applying signal processing to the collected data.

CD-SEM (CDSEM)—Critical Dimensions Scanning Electron Microscope, which is applicable in a wide range of nodes having dimensions from about 3000 nm to about 5 nm. CD-SEM delivers High Resolution, High Throughput, and High Repeatability by utilizing improved electron optics and advanced image processing.

CAD data—design data obtained from a CAD-image created by utilizing CAD (computer-aided design) tools for designing features of a specific layer of a wafer.

DR-SEM (Defect Review SEM)—SEM intended for localization of defects on semiconductor wafers, uses an approach of comparing images and does not include performing measurements with high resolution.

Grey Scale Image/Grey Level Image—a digital image/images in the range $[0\text{-}(2^{8N}-1)]$ of an object to be analyzed, obtained by SEM or CD-SEM. The Grey level image may be obtained using technologies of SE or BSE.

Semiconductor wafer—a semiconductor structure having at least one layer formed by a plurality of features deposited onto the structure.

Via In Trench technology (VIT), Dynamic Random-Access Memory technology (DRAM), Vertical NAND [Negative-AND gate] logic gate technology (VNAND)—modern technologies characterized by a so-called HAR (High Aspect Ratio), which expresses quite high ratio of height/width for a feature to be measured. These technologies are therefore characterized by complex relief of the features created by them and by difficulties of controlling shape of the features by presently known techniques such as SE.

Presently, when technologies up to 8 nm have already emerged and more advanced technologies are being developed, there is a need for a cost-effective, precise, high throughput, non-destructive, high resolution technique of controlling fabrication of semiconductor wafers.

SUMMARY

Aspects of the present disclosure provide a method for detecting material properties and/or defects of semiconductor wafers. The method comprises concurrently performing CD-SEM measurements of a semiconductor wafer, and analysis of a Grey Level image of the wafer, obtained by a material-sensitive and HAR-sensitive imaging technology; and processing together results of the CD-SEM measurements of the semiconductor wafer, and the analysis of the Grey Level image of the wafer, obtained by the material-sensitive and HAR-sensitive imaging technology.

In some implementations, the method may further comprise automatically inspecting the semiconductor wafer, by performing BSE imaging for obtaining the Grey Level image (GL) of the wafer, analysis of the obtained GL, concurrently with CD-SEM measurements of the semiconductor wafer, and processing results of the CD-measurements together with results of the GL analysis, to determine material properties and/or defects of said wafer. The CD-SEM measurements can also be performed using a Grey Level image created by the BSE imaging.

In some implementations, the method may further comprise detecting defectivity of the semiconductor wafers' fabrication process, based on the material properties and/or defects determined for the wafer, to enable control of the fabrication process. The semiconductor wafers can be manufactured according to one or more of technologies characterized by High Aspect Ratio (HAR), the technologies comprising VIT, DRAM, VNAND.

In some implementations, performing the GL analysis comprises determining one or more of the following parameters of a feature or group of features fabricated on the semiconductor wafer: Uniformity, Contrast, or Statistical characteristics of Quality Grades of contours of the feature. The GL analysis may include one or more of the following: GL uniformity analysis, for detecting defects inside features, GL analysis of relative Contrast of layers, for detecting material property of layers, or Fit-Quality analysis of GL based on GL statistics, for detecting missing features by analyzing feature contours location and primary knowledge. In some implementations, the GL analysis can be performed upon Inverse Transformation per pixel of the Grey Level image, by recovering original data on BSE signals previously transformed to produce the Grey-Level image.

In some implementations, the method may also comprise executing the Inverse Transformation of the Grey Level image per pixel by Grey-Level Stretching Compensation, while said Transformation comprised Grey-Level image Stretching. In some implementations, the method may further comprise obtaining one or more Grey Level threshold values, using the recovered original data on physical signals, and utilizing the threshold values for determining defects.

In some implementations, performing the BSE measurements comprises determining uniformity of a specific feature by using Gray Level Uniformity (GLU) analysis by estimation of Grey Level distribution on the features' area. In some implementations, the method also comprises determining contrast of a feature by comparing Gray Level statistical metrics m and a, obtained upon the BSE Imaging, with CD measurements based on a number of similar features. In some implementations, the method further comprises determining presence/absence of a feature on the semiconductor wafer by Fit Quality analysis of feature contours location based on Gray Level image statistics and primary knowledge.

According to some aspects of the disclosure. a Critical Dimensions Scanning Electron Microscope (CD-SEM) is provided that comprises a unit for performing CD-SEM measurements of a semiconductor wafer; a BSE imaging unit for obtaining a Grey Level image (GL) of the wafer, and a unit for GL analysis and for processing the GL analysis results with reference to results of the CD-measurements. The CD-SEM can also comprise a block for providing primary knowledge on features' location on the wafer. The CD-SEM can further comprise BSE detectors for collecting BSE-data for the BSE-imaging.

In some implementations, the unit for GL analysis is configured to perform Inverse Transformation of the GL image to restore original BSE data on physical signals. In some implementations, the unit of GL analysis is configured to respectively perform measurements of Uniformity, Contrast, Contours of a feature or group of features fabricated on the semiconductor wafer, based on the restored original BSE data. In some implementations, the CD-SEM further comprises a unit for detecting material properties and defects of the semiconductor wafer based on the one or more measurements of Uniformity, Contrast, Contours of the feature or group of features.

It should be noted that the details and the options described above with reference to the inventive method, are also applicable to the inventive CD-SEM.

According to a further aspect of the invention, there is also provided a software product comprising computer implementable instructions and/or data for carrying out the method described above, stored on an appropriate computer readable non-transitory storage medium so that the software is capable of enabling operations of the method when used in a computer system (for example—in the proposed CD-SEM).

Versions and embodiments of the CD-SEM technology will be described in more detail with reference to the attached drawings.

BRIEF DESCRIPTION OF THE DRAWINGS

Embodiments of the invention will be further explained and illustrated with the aid of the following non-limiting drawings in which.

DETAILED DESCRIPTION OF SPECIFIC EMBODIMENTS

Figure 1:
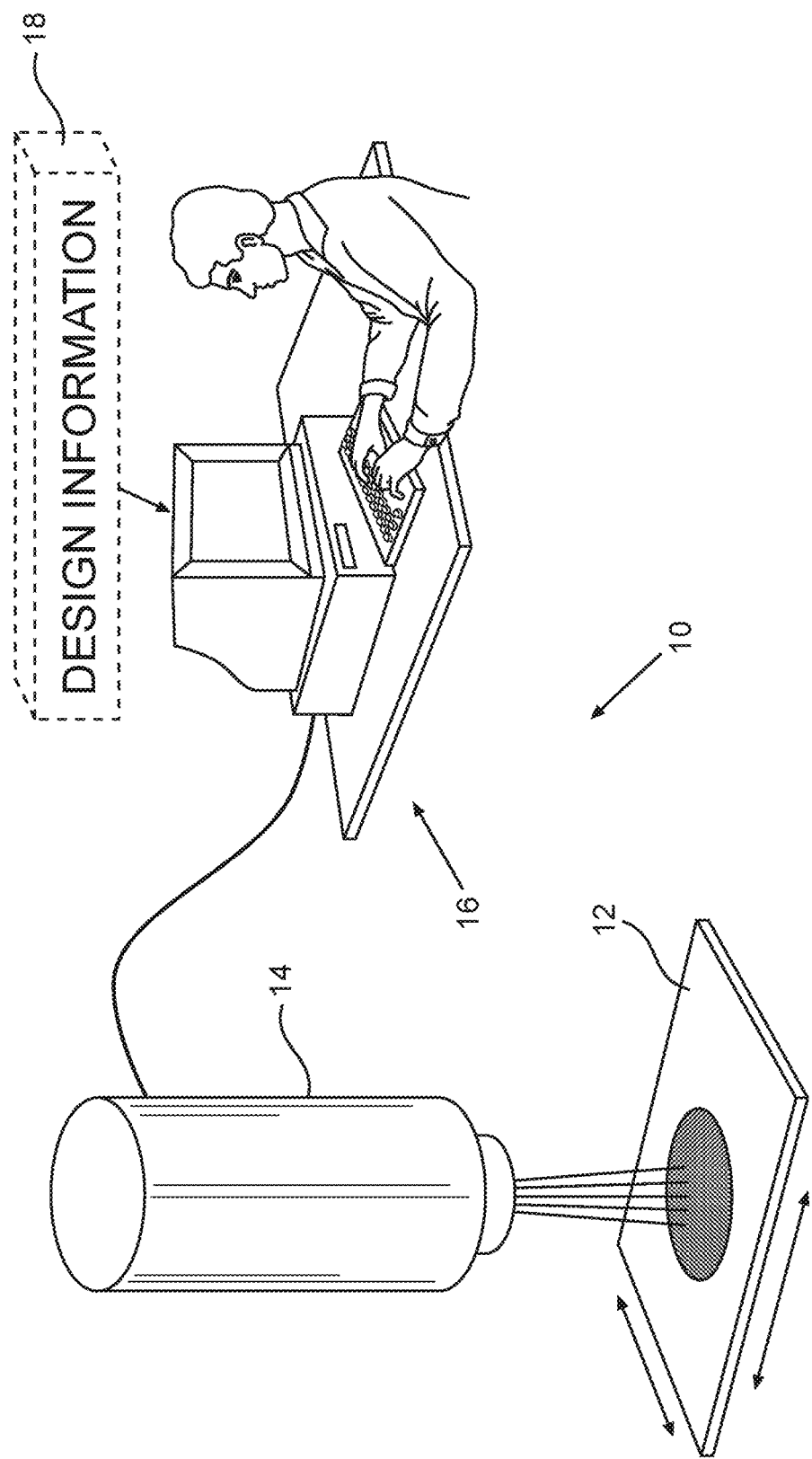
FIG. 1 schematically illustrates an embodiment of the proposed CD-SEM for performing the inventive method.

As discussed above, regular CD-SEM measurements (CD Metrics) may not be enough for process control of modern semiconductor wafers production. The proposed new CD SEM Edgeless Metrology Segmentation based methods, performed simultaneously with CD-SEM geometric analysis, open new possibilities for analysis of fine structure of features and patterns formed by the features.

Aspects of the present disclosure provide a technology for fabrication process control of modern semiconductor wafers, and in particular a new approach to effective inspection of shape, material properties and defects in features fabricated on the semiconductor wafers. Aspects of the disclosure make inspection of such issues of the fabricated features as part of the CD-measurements based process control. The enhanced process control therefore allows improving both the process development cycle and the manufacturing cycle.

Aspects of the disclosure can gather exact required information for any certain material compound and any required shape on a semiconductor wafer for controlling a process of semiconductor wavers fabrication, by providing a CD-SEM technology comprising a CD-SEM metrology analysis, together with a technique such as Back Scattered Electron Imaging (BSE imaging), and utilizing the BSE Imaging analysis inline with CD-SEM metrology analysis, thereby creating both a combined process control technology and a novel method for wafers inspection. (It should be noted that a CD-SEM metrology analysis can be based on SE imaging but the use of the SE imaging is not obligatory.)

According to some aspects of the disclosure, a method is provided for detecting material properties and/or defects of semiconductor wafers (or monitoring thereof during their fabrication), by concurrently performing and processing together results of CD-SEM measurements of a semiconductor wafer, and analysis of a Grey Level image of the wafer obtained by material sensitive and HAR-sensitive imaging, such as BSE imaging or the like. The method of detecting/monitoring material properties and/or defects therefore serves the basis of a novel method for process control and a novel method of wafers inspection, aspects of which will be described below.

It will further be described that aspects of the disclosure present those new techniques of inspection and faster process control by using so-called BSE mass data mining. The BSE data mining will allow developing the faster process cycle instead of sending wafers for destructive material analysis.

According to a first aspect of the invention, a method is provided for automatically inspecting a semiconductor wafer (preferably during a fabrication process), by performing:

BSE imaging or the like for obtaining a Grey Level image (GL) of the wafer, analysis of the obtained GL, concurrently with CD-SEM measurements of the semiconductor wafer, processing results of the CD-measurements together with results of the GL analysis, thereby determining material properties and/or defects of said wafer.

It should be noted that the term "BSE-imaging or the like" should be understood as a present or future imaging technology which is material-sensitive and HAR-sensitive. Owing to those possibilities, such imaging enables determination of material properties and defects (if any) of a semiconductor wafer characterized by HAR, upon performing analysis of the Grey Level image obtained by such imaging technology, and while using results of CD-SEM measurements in the analysis.

The CD-SEM measurements preferably utilize primary knowledge about features' location on the wafer, which primary knowledge is usually provided by a design data (for example, CAD data). The analysis of the BSE-based Grey Level image may comprise performing one or more of GL analysis algorithms which, in the frame of the present description, will be called BSE-related measurements or just BSE measurements, for example:

GL uniformity analysis (for detecting defects inside features),

GL analysis of relative contrast of layers (for detecting material properties of layers), Fit-Quality analysis of GL based on GL statistics (for detecting missing features by analyzing feature contours location and primary knowledge).

As mentioned above, and despite the fact that the above-mentioned GL analysis (or BSE measurements) has a significant Process Control value for BSE images due to direct relation between BSE signal and material properties of the wafers' features, these measurements can be applicable also to SE-images or any other related to wafer fabrication images, if such images formation is material sensitive and HAR sensitive. The method may further comprise detecting defectivity (blunders) of the fabrication process based on the material properties and/or defects determined for the wafer, thereby enabling control of the fabrication process.

In terms of a device, a novel CD-SEM is provided that is capable of performing CD-SEM measurements of semiconductor wafers (i.e., having its conventional unit for CD-SEM measurements of a semiconductor wafer), The CD-SEM can include a unit for obtaining a Grey Level image (GL) of the wafer by BSE (or the like) imaging, and a unit for analysis of the obtained GL, and for concurrently processing the analysis results with those of the CD-measurements, to determine material properties and/or defects of said wafer. The unit for CD-SEM measurements needs some design input data, so it may be connected to a CAD unit, to receive CAD input data from.

The proposed novel combination of two analytic approaches (i.e., CD-SEM metrology and BSE or the like imaging defectology) allows obtaining a complete set of features parameters, which integrate precision of conventional CDSEM measurements concerning the features shape, with new information about features uniformity and contrast. This new information is obtained concurrently with said CD-SEM measurements, by creating the Grey Level image using the mentioned BSE technology and by novel processing of said Grey Level image.

The CD-SEM measurements may be also performed using the Grey Level image created by the BSE technology. The BSE technology can be, for example an LL-BSE technology. Alternatively, the CD-SEM measurements may be performed using SE imaging.

The semiconductor wafer, inter alia, may be manufactured according to at least one of the following novel technologies characterized by the so-called High Aspect Ratio (HAR): VIT, DRAM, VNAND, etc. More specifically, in some embodiments, the BSE measurements may be performed upon Inverse Transformation processing, i.e. upon reverse calculation of the number of electrons from each pixel of a Grey Level image obtained by BSE imaging.

The proposed BSE measurements (i.e., the Grey Level analysis) are performed in the framework of so-called Edge-less Metrology Segmentation Based algorithms (for comparison, conventional CD-SEM measurements based on SE technology belong to the conventional Edge Segmentation approach).

The BSE measurements may include determining one or more of the following parameters of a feature or group of features fabricated on a semiconductor wafer: Uniformity, Contrast, Presence/Absence (Statistical characteristics of quality of contours) of the feature. Accordingly, the GL analysis (the BSE or the like measurements) may include, for example, the following types of measurements:

a) Grey Level uniformity analysis, based on Gray Level distribution inside a specific feature (which allows determining defects inside of the feature);
b) Grey Level based Contrast analysis of a feature relatively to Contrast from other layers, reflecting material properties of layer surfaces (which provides comprehensive info for any combinations of the layers seen in the GL image; in particular—reflects and allows determining sufficiency, density and/or homogeneity of the material distribution inside the feature); and/or
c) Fit Quality analysis of feature Contours based on GL statistics (which allows detecting missing or disappearing features by combining CAD data analysis).

In some implementations, for any of the above-mentioned types of BSE measurements, initial/original data on physical signals (BSE signals) is obtained. In other words, the Grey level analysis (the BSE measurements) may comprise Inverse Transformation, per pixel, of the Grey-Level image, by recovering original data on physical signals (BSE signals) previously transformed to produce the Grey-Level image, thereby preserving the Grey Level image and obtaining the recovered original data—for estimation of Grey Level statistical metrics (m and a, see below) and for further determining material properties and defects.

In the method/device, the original data on physical signals may be understood as data related to electrons initially collected by BSE sensors from the wafer per pixel of the Grey Level image which is created from the original data by using the Back Scattered Electron (BSE) imaging (for example, by Low Loss Back Scattered Electron (LL BSE) imaging).

As mentioned above, the recovery of the original data on physical BSE signals may be performed by executing a so-called Inverse Transformation of the Grey-Level image per pixel. The Inverse Transformation comprises Grey-Level Stretching Compensation, while said transformation itself comprised Grey-Level image Stretching.

The Grey Level Image (GL) Stretching may be performed according to the following equation, describing transformation of the initial signal into an image being 8*N bits long:

$Y=a*V+b$, where $Y(x,y)=a*V(x,y)=b$ $a=(2^{8N}-1)/(V_{max}-V_{min})$;

$b=-V_{min}(2^{8N}-1)/(V_{max}-V_{min})$ and where
x, y—are a pixel coordinates of the image,
Y (x, y)—is the 2D GL signal (defining image) after stretching,
V (x, y)—the 2D GL signal (defining image) before stretching after frames summation, i.e., the number of BSE electrons in each pixel of the image (which image will be obtained after the transformation/stretching),
$V_{max}$—the maximum of 2D GL signal before stretching,
$V_{min}$—the minimum of 2D GL signal before stretching.

The stretching of GL for estimation of statistical parameters may then be compensated in a function called, for example, "create CDResults" by using the following formulae:

$m=(m-b)/a$; where $m$ is a mean (average) Grey Level in image region, $\sigma=\sigma/a$; where $\sigma$ is Standard Deviation of Grey Level in image region The stretching parameters $V_{max}$, $V_{min}$ may be preserved during image formation, and the values of m and σ may then be used for further manipulations with the Grey Level Image. Correct values of m and σ may be obtained for a specific image region (without recovery of the whole image data), thus obtaining one or more reference regions for further GL analysis.

The method may further comprise obtaining one or more threshold values, using the recovered original data on physical BSE signals, and utilizing the threshold values for determining defects during the BSE measurements.

We are now to discuss in more details the three above-mentioned types a, b, c of the defectivity analysis, i.e., three exemplary ways of determining defects by BSE measurements of Uniformity, Contrast, Contours of the feature on the Grey Level Image. The exemplary types of analysis are applicable both in terms of the proposed method (as sub-steps of the BSE measurements), and in terms of the proposed device, for example as optional software units thereof.

Uniformity of a specific feature may be determined using so-called Grey Level Uniformity (GLU) analysis by estimation of Grey Level distribution on a features' area. The Grey Level uniformity can be estimated as a relative deviation of the grey level in the local window around each pixel from the average grey level of the feature in the units of standard deviation.

In the method/device, Contrast of a feature may be determined by comparing Gray Level metrics (m and σ) for each feature, obtained upon the BSE Imaging using CD measurements based on a number of similar features; for example, the contrast is determined by Gray Level statistics, as a relative contrast obtained based on comparing brightness of the feature and of any unchangeable background. For example, the m and σ of members of a group of similar features on the wafer may be compared with the m and σ of the upper layer of the wafer. These comparisons can be performed for all layers existing on the Grey level image, thus providing comprehensive information about material properties on the wafer for the process control. Presence/Absence of a feature on a semiconductor wafer may be determined by a so-called Fit Quality analysis of Contours of the feature based on the Gray Level statistics.

In some implementations, the Fit Quality procedure is based on an assumption that a feature contour, found in CD measurements with the use of Primary knowledge (such as CAD information), separates two statistically different distributions on the image. If the distributions are different, any statistical criterion (e.g. the Kolmogorov-Smirnov criterion) can be used to allow defining exact locations of the missing features.

Therefore, in some implementations, owing to the proposed Grey Level analysis (BSE measurements), performed concurrently with the CD-SEM measurements, the method may be adapted for control of features' geometry with determining defects, material's distribution homogeneity, and material composition of patterns on a layer of the structure.

According to a second aspect of the invention, there is provided a novel CD SEM designed for performing the method described above. As mentioned before, it is a CD-SEM having a unit for performing CD-SEM measurements of a semiconductor wafer; a BSE imaging unit for obtaining a Grey Level image (GL) of the wafer; and a unit for GL analysis and for processing the GL analysis results with reference to results of the CD-measurements, so as to allow determining material properties and/or defects of said wafer.

The CD-SEM may preferably comprise a block for providing primary knowledge on features' location on the wafer (for example, CAD images). The proposed CD-SEM may incorporate BSE detectors for collecting BSE-data for the BSE-imaging. As already mentioned, the BSE imaging technology (with reference to the proposed CD-SEM) should be understood as BSE or another technology being both material-sensitive and HAR sensitive so as to allow obtaining such a GL image which upon analysis with the CD-SEM measurement, would allow determining material properties and defects of semiconductor wafers.

The CD-SEM may further comprise a unit for detecting material properties and defects of the semiconductor wafer. The unit may be especially configured by a specific user and be therefore an additional unit tailored and allocated separately from the CD-SEM. The CD-SEM may also comprise a displaying unit for visualizing and reporting the processing results.

The GL analysis and processing unit may comprise a software block configured to perform Inverse Transformation of the GL image to restore original BSE data on physical signals. The GL analysis and processing unit may comprise one or more of the following hardware-software blocks configured to respectively perform measurements of Uniformity, Contrast, Contours of a feature or group of features fabricated on a semiconductor wafer, based on the restored original BSE data. The GL analysis and processing unit may further comprise a block for determining material properties and/or defects based on the obtained said measurements of Uniformity, Contrast, Contours of the feature.

Figure 2:
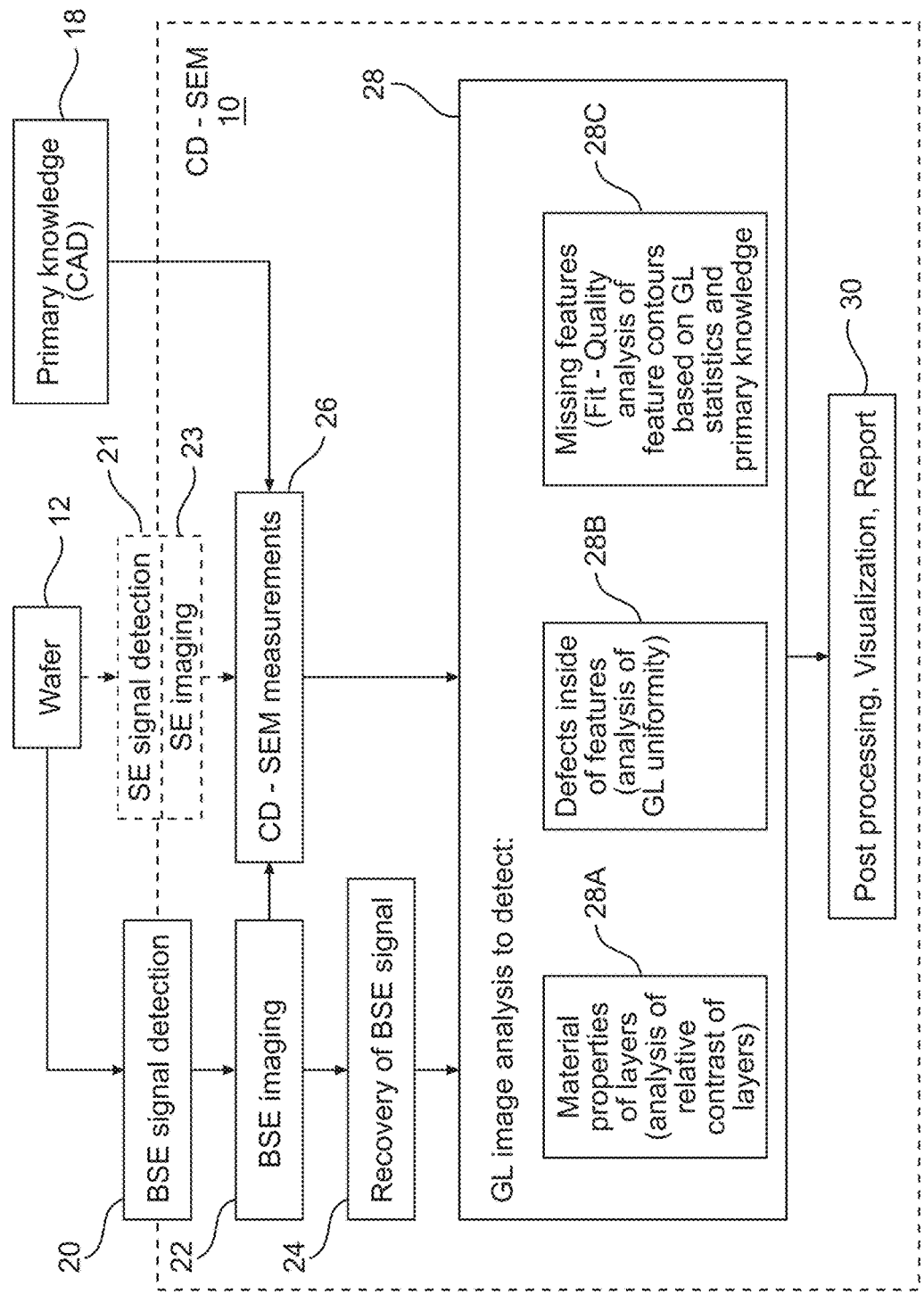
FIG. 2 illustrates a schematic block diagram of another embodiment of the novel CD-SEM.

FIG. 1 schematically illustrates one embodiment of the proposed CD-SEM 10 for performing some implementations of the inventive method. In FIG. 1, the object of inspection during the process control is a semiconductor wafer 12, which moves under an elongated Electron block 14 holding a source of electrons' beam and a set of electrons' sensors (not seen). For example, the set may comprise a combination of SE and BSE sensors. The moving wafer 12 gradually exposes its relief to the electron beam and to the combination of SE and BSE sensors. The illustrated embodiment 10 of the CD-SEM comprises the external Electron block 14 with a set of sensors and a processor (the computer 16) incorporating both the facilities for performing the CD-SEM measurements and the facilities for concurrently performing GL analysis (BSE measurements). In one present example of CD-SEM, all the measurements are performed based on BSE data received from the BSE sensors. Block 18 schematically illustrates that in the processing of the CD-SEM measurements and the BSE measurements, the processor of computer 16 may also utilize primary knowledge (design information, such as CAD data) concerning the wafer 12. An example computer 16 implementing methods discussed in the present disclosure is described in more detail in conjunction with Figure FIG. 2 illustrates a schematic block diagram of another and more detailed embodiment of the novel CD-SEM 10. The block diagram of FIG. 2 may also serve an exemplary flow chart of the proposed method. In this embodiment, a BSE detectors unit 20 is an inner part of CD-SEM. An SE detectors unit 21 and an SE Imaging unit 23 are shown as optional units. The proposed novel CD-SEM 10 may utilize and process data received at least from the BSE detection unit 20. FIG. 2 shows the following functional blocks of the CD-SEM 10, intended for providing: Primary knowledge (18), BSE signal detection (20), BSE imaging (22), Recovery of BSE signal (24), CD-SEM measurements (26), Grey Level Image analysis (28) using results of the CD-SEM measurements and primary knowledge, and a block (30) of Post processing, Visualization and Report. In the present example, the Grey Level analysis (28) comprises performing the following BSE measurements to detect: Material properties of deep layers (block 28A), Defects inside the features (block 28B), Missing features (block 28C).

Figure 3B:
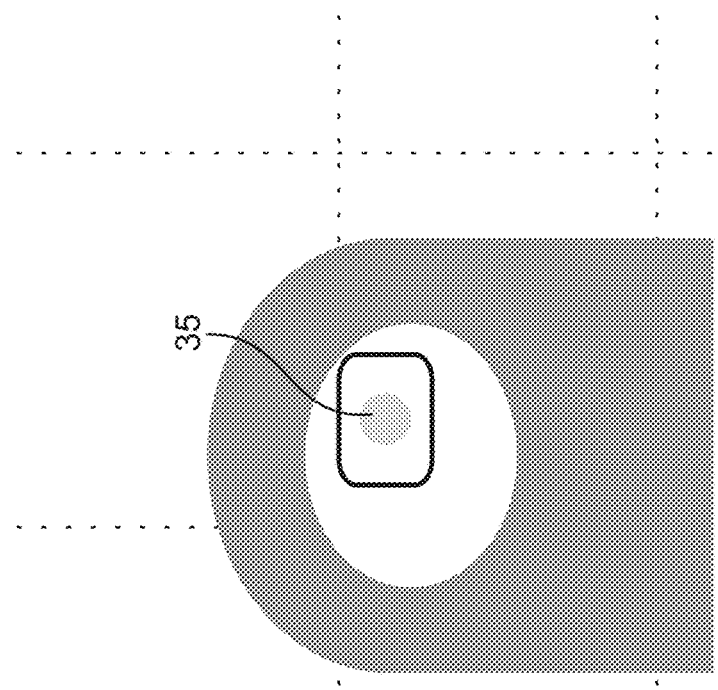
FIGS. 3A and 3B—pictorial illustration of a feature and of its enlarged portion, showing capability of the proposed CD-SEM to detect and analyze non-uniformity of a pattern fabricated on a wafer, by performing and using BSE measurements, in accordance with some embodiments.
Figure 3A:
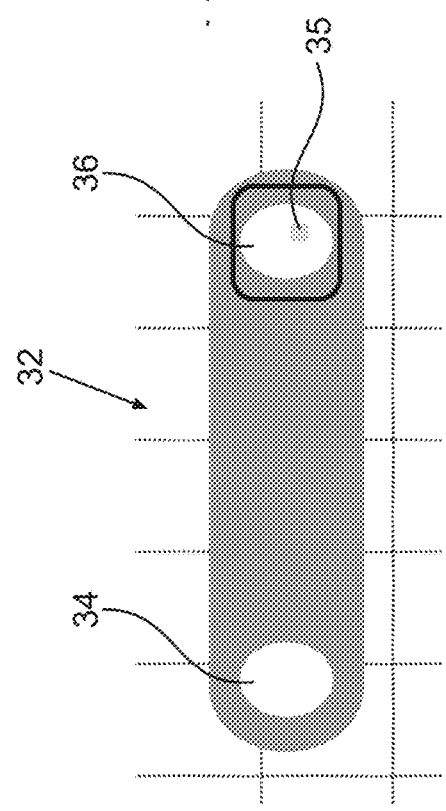

FIGS. 3A and 3B demonstrate capability of the proposed CD-SEM to perform BSE measurements so as to detect and analyze non-uniform patterns. FIG. 3A is a pictorial illustration of a specific feature 36 (being a lower layer portion, seen through a hole in feature 32) fabricated on a wafer, and FIG. 3B—of an enlarged portion of the feature 36. It shows how non-uniformity of a pattern fabricated on a wafer can be detected using BSE measurements defining a feature shape. The non-uniform pattern 35 is marked with a rectangular frame both on the feature and on its enlarged image. The non-uniform pattern 35 was detected using the algorithm, which allows performing Grey Level Uniformity (GLU) analysis, i.e. estimation of the Grey Level and the defect area statistics of the non-uniform patterns.

Figure 4A:
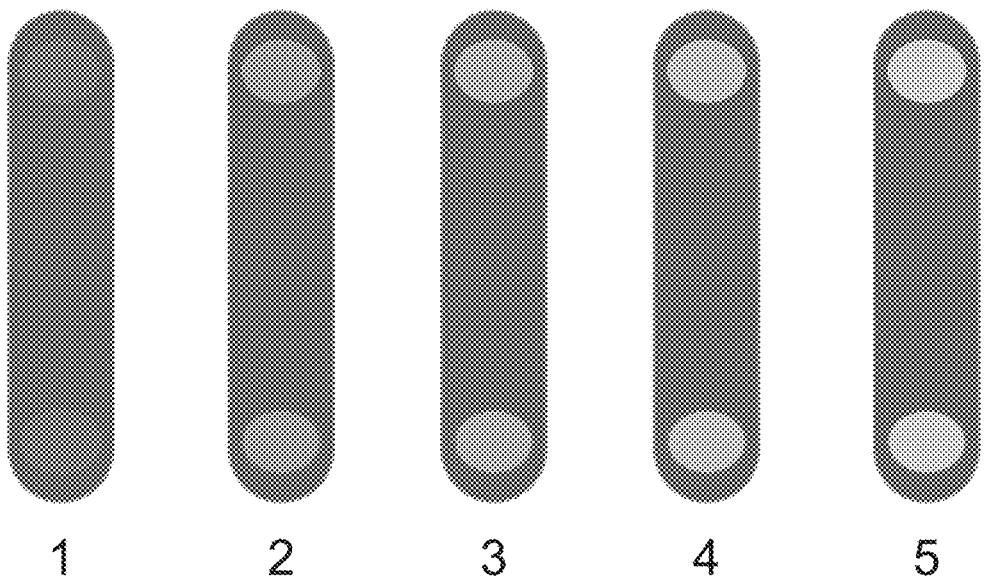
FIGS. 4A, 4B comprise an exemplary Grey Level photo and a diagram showing how Grey Level analysis can be used for estimating and then explaining different contrast values detected for different features, in accordance with some embodiments.
Figure 4B:
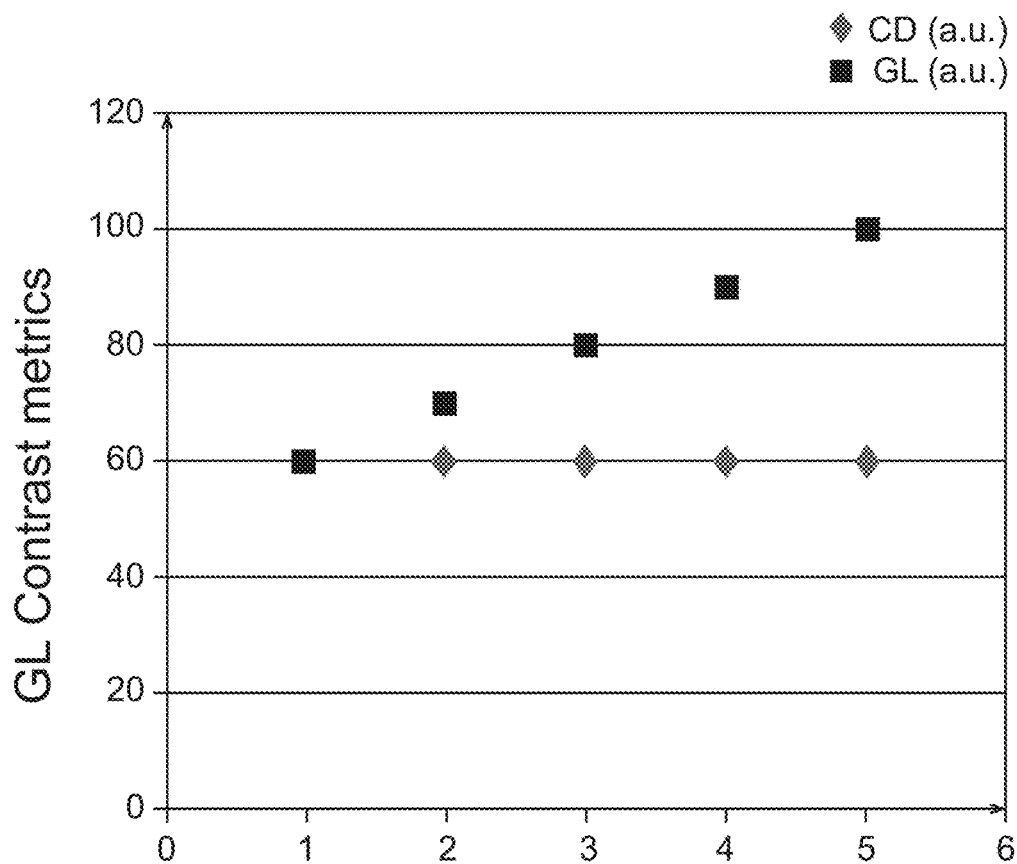

FIGS. 4A, 4B comprise an exemplary Grey Level photo and a diagram showing how Grey Level analysis can be used for estimating and then explaining different contrasts detected for different features on a wafer. The features are numbered 1, 2, 3, 4, 5. It should be noted that the features may have similar CD (critical dimensions), as can be seen in FIG. 4A. The features 1, 2, 3, 4, 5 of a group shown in FIG. 4A have the same Critical Dimension (CD), but different Gray Level (GL) metrics estimating contrast of a feature compared to some specific reference layer. Results of the CD and BSE measurements can be seen in FIG. 4B. The novel Process Control is conducted, with simultaneously performing both the Grey Level Analysis using BSE measurements, and the CD analysis for the same features 1, 2, 3, 4, 5: see rectangular marks of GL in FIG. 4B, obtained in GL arbitrary units; see also corresponding rhomboid CD marks in FIG. 4B, obtained in CD arbitrary units (a.u.).

The mentioned comparison for detecting features' contrast can be performed for all layers existing on the Grey Level image, thus providing comprehensive information, for the process control, about material properties of layers of interest on the wafer.

Figure 5B:
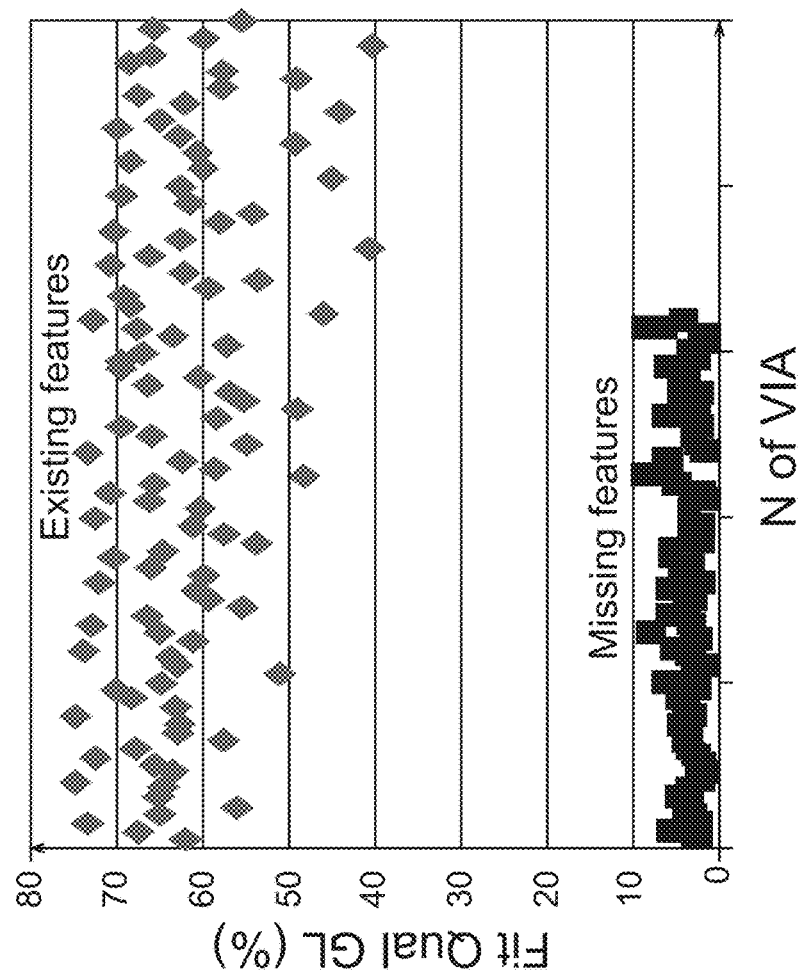
FIGS. 5A, 5B comprise an exemplary Grey Level image and a diagram illustrating how the BSE measurements can be used for detecting a missing pattern, in accordance with some embodiments.
Figure 5A:
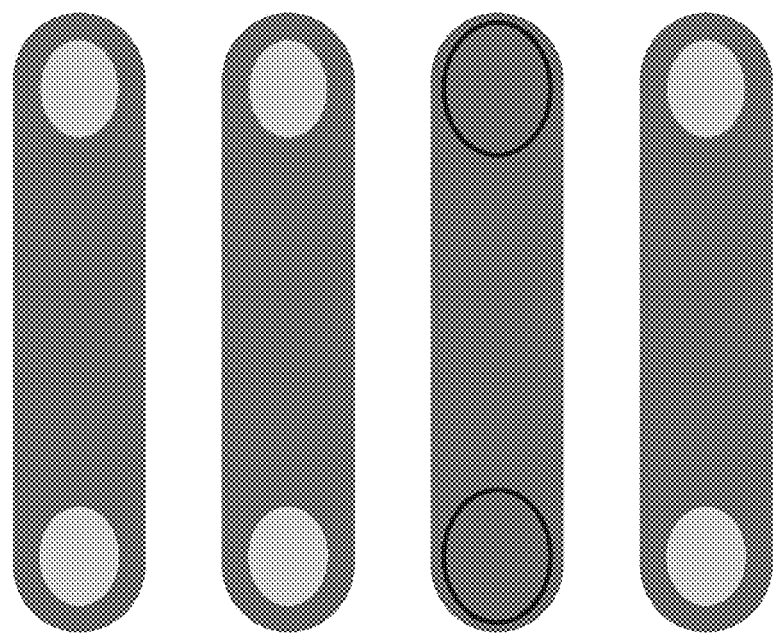

FIGS. 5A, 5B comprise an exemplary Grey Level image of features and a diagram illustrating how the BSE measurements can be used for detecting a missing pattern. FIG. 5B shows how the so-called Fit Quality Analysis can be used for missing features detection. For example, two missing features are marked in FIG. 5A by black elliptic frames around dark grey areas on longitudinal features—see the third longitudinal feature (let the feature be VIA) from above. On the plane between the axis of Fit Quality grades of Grey Level image (in %) and the axis of number (N) of VIAs, the missing features have well separated Fit Quality grades vs Fit Quality grades of existing features. In FIG. 5B, the lower part of the diagram is fully packed with square-like points corresponding to Fit Quality grades of missing features for some VIAs on the wafer, while the upper side of the diagram 5B is populated only by rhomboid points which mark Fit Quality grades of existing features. For any specific N of VIAs, the sum of existing features and missing features is constant (known in advance from the design information). The number N of VIAs and the number of missing features in FIG. 5B does not have to obligatory correspond to those in FIG. 5A (FIG. 5A only serves for illustrating a specific defective VIA).

In this case CD measurements, based on primary knowledge about designed location of features of interest (say, from CAD image—see FIG. 2) serve as a reference for the GL analysis. While serving a reference, CD measurements almost do not contribute data for detecting defects, since CD measurements are unable to measure a feature which does not exist.

Figure 6:
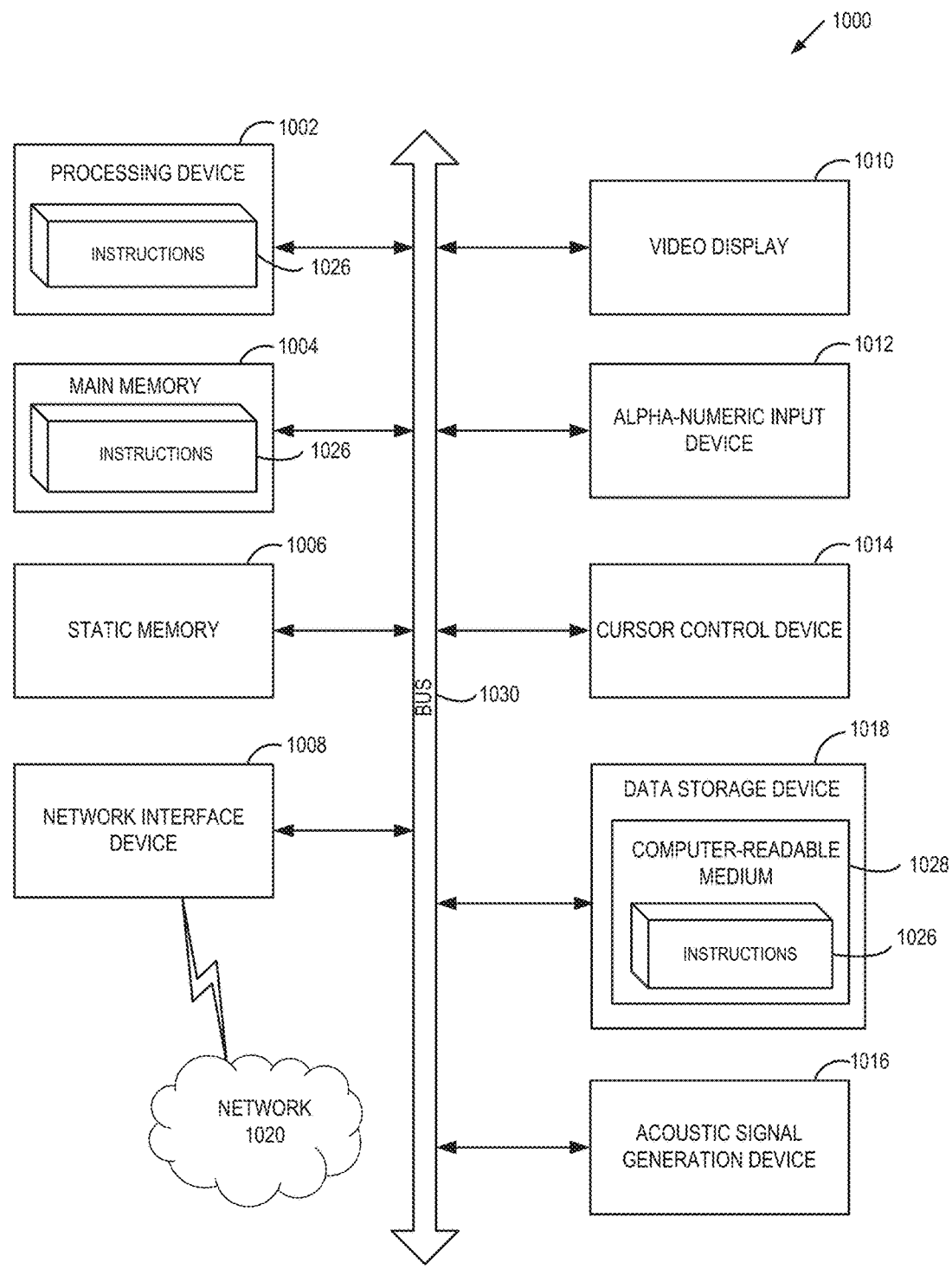
FIG. 6 depicts a block diagram of an example computer system operating in accordance with one or more aspects of the present disclosure.

FIG. 6 schematically illustrates a component diagram of an example computer system 1000 which may perform any one or more of the methods described herein. In various illustrative examples, computer system 1000 may represent a computer 16 of FIG. 1. Example computer system 1000 may be connected to other computer systems in a LAN, an intranet, an extranet, and/or the Internet. Computer system 1000 may be a personal computer (PC), a set-top box (STB), a server, a network router, switch or bridge, or any device capable of executing a set of instructions (sequential or otherwise) that specify actions to be taken by that device. Further, while only a single example computer system is illustrated, the term "computer" shall also be taken to include any collection of computers that individually or jointly execute a set (or multiple sets) of instructions to perform any one or more of the methods discussed herein.

Example computer system 1000 may comprise a processing device 1002 (also referred to as a processor or CPU), a main memory 1004 (e.g., read-only memory (ROM), flash memory, dynamic random access memory (DRAM) such as synchronous DRAM (SDRAM), etc.), a static memory 1006 (e.g., flash memory, static random access memory (SRAM), etc.), and a secondary memory (e.g., a data storage device 1018), which may communicate with each other via a bus 1030.

Processing device 1002 represents one or more general-purpose processing devices such as a microprocessor, central processing unit, or the like. More particularly, processing device 1002 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1002 may also be one or more special-purpose processing devices such as an application specific integrated circuit (ASIC), a field programmable gate array (FPGA), a digital signal processor (DSP), network processor, or the like. In accordance with one or more aspects of the present disclosure, processing device 1002 may be configured to execute instructions 1026 implementing methods discussed herein.

Example computer system 1000 may further comprise a network interface device 1008, which may be communicatively coupled to a network 1020. Example computer system 1000 may further comprise a video display 1010 (e.g., a liquid crystal display (LCD), a touch screen, or a cathode ray tube (CRT)), an alphanumeric input device 1012 (e.g., a keyboard), a cursor control device 1014 (e.g., a mouse), and an acoustic signal generation device 1016 (e.g., a speaker).

Data storage device 1018 may include a computer-readable storage medium (or more specifically a non-transitory computer-readable storage medium) 1028 on which is stored one or more sets of executable instructions 1026. In accordance with one or more aspects of the present disclosure, executable instructions 1026 may comprise executable instructions encoding various functions of methods 500 and/or 600 for file sharing over secure connections.

Executable instructions 1026 may also reside, completely or at least partially, within main memory 1004 and/or within processing device 1002 during execution thereof by example computer system 1000, main memory 1004 and processing device 1002 also constituting computer-readable storage media. Executable instructions 1026 may further be transmitted or received over a network via network interface device 1008.

While computer-readable storage medium 1028 is shown in FIG. 6 as a single medium, the term "computer-readable storage medium" should be taken to include a single medium or multiple media (e.g., a centralized or distributed database, and/or associated caches and servers) that store the one or more sets of VM operating instructions. The term "computer-readable storage medium" shall also be taken to include any medium that is capable of storing or encoding a set of instructions for execution by the machine that cause the machine to perform any one or more of the methods described herein. The term "computer-readable storage medium" shall accordingly be taken to include, but not be limited to, solid-state memories, and optical and magnetic media.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "identifying," "determining," "storing," "adjusting," "causing," "returning," "comparing," "creating," "stopping," "loading," "copying," "throwing," "replacing," "performing," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Examples of the present disclosure also relate to an apparatus for performing the methods described herein. This apparatus may be specially constructed for the required purposes, or it may be a general purpose computer system selectively programmed by a computer program stored in the computer system. Such a computer program may be stored in a computer readable storage medium, such as, but not limited to, any type of disk including optical disks, CD-ROMs, and magnetic-optical disks, read-only memories (ROMs), random access memories (RAMs), EPROMs, EEPROMs, magnetic disk storage media, optical storage media, flash memory devices, other type of machine-accessible storage media, or any type of media suitable for storing electronic instructions, each coupled to a computer system bus.

The methods and displays presented herein are not inherently related to any particular computer or other apparatus. Various general purpose systems may be used with programs in accordance with the teachings herein, or it may prove convenient to construct a more specialized apparatus to perform the required method steps. The required structure for a variety of these systems will appear as set forth in the description below. In addition, the scope of the present disclosure is not limited to any particular programming language. It will be appreciated that a variety of programming languages may be used to implement the teachings of the present disclosure.

It is to be understood that the above description is intended to be illustrative, and not restrictive. Many other implementation examples will be apparent to those of skill in the art upon reading and understanding the above description. Although the present disclosure describes specific examples, it will be recognized that the systems and methods of the present disclosure are not limited to the examples described herein, but may be practiced with modifications within the scope of the appended claims. Accordingly, the specification and drawings are to be regarded in an illustrative sense rather than a restrictive sense. The scope of the present disclosure should, therefore, be determined with reference to the appended claims, along with the full scope of equivalents to which such claims are entitled.

We claim:

1. A method for detecting material properties and/or defects of semiconductor wafers, the method comprising:
   concurrently performing operations to obtain Critical Dimensions Scanning Electron Microscope (CD-SEM) measurements of a semiconductor wafer and an analysis of a Grey Level image of the semiconductor wafer, by a material-sensitive and High Aspect Ratio (HAR)-sensitive imaging technology; and
   processing together results of the CD-SEM measurements of the semiconductor wafer and the analysis of the Grey Level image of the wafer obtained by the material-sensitive and HAR-sensitive imaging technology.

2. The method of claim 1, further comprising:
   automatically inspecting the semiconductor wafer by:
   performing Back Scattering Electron (BSE) imaging to obtain the Grey Level (GL) image of the semiconductor wafer;
   performing an analysis of the obtained GL image concurrently with the CD-SEM measurements of the semiconductor wafer; and
   processing results of the CD-SEM measurements together with results of the GL image analysis to determine material properties and/or defects of the semiconductor wafer.

3. The method of claim 2, wherein the CD-SEM measurements are further obtained by using the Grey Level image created by the BSE imaging.

4. The method of claim 2, further comprising:
   detecting defectivity of a fabrication process of the semiconductor wafer based on the material properties and/or defects determined for the semiconductor wafer to enable control of the fabrication process.

5. The method of claim 2, wherein performing the GL image analysis comprises:
   determining one or more of the following parameters of a feature or group of features fabricated on the semiconductor wafer: Uniformity, Contrast, or Statistical characteristics of Quality Grades of contours of the feature.

6. The method of claim 5, wherein performing the GL image analysis comprises:
   determining of uniformity of a specific feature by using Gray Level Uniformity (GLU) analysis by estimation of Grey Level distribution on an area of the specific feature.

7. The method of claim 5, further comprising:
   determining contrast of the feature by comparing Gray Level statistical metrics corresponding to an average of a Grey Level in a region of the GL image and a standard deviation of the Grey Level in the region of the GL Image that are obtained upon the BSE imaging with CD-SEM measurements based on a number of similar features.

8. The method of claim 5, further comprising:
   determining a presence or an absence of a particular feature on the semiconductor wafer by Fit Quality analysis of feature contours location based on Gray Level image statistics and primary knowledge.

9. The method of claim 2, wherein the GL image analysis includes one or more of the following:
   GL uniformity analysis to detect defects inside features;
   GL analysis of relative contrast of layers to detect material property of layers; or
   Fit-Quality analysis of the GL image based on GL statistics to detect missing features by analyzing feature contours location and primary knowledge.

10. The method of claim 2, wherein the GL image analysis is performed upon Inverse Transformation per pixel of the Grey Level image by recovering original data on BSE signals previously transformed to produce the Grey-Level image.

11. The method of claim 10, further comprising:
    executing the Inverse Transformation of the Grey Level image per pixel by Grey-Level Stretching Compensation while the Inverse Transformation comprised Grey-Level image stretching.

12. The method of claim 10, further comprising:
    obtaining one or more Grey Level threshold values by using the recovered original data on physical signals; and
    utilizing the one or more Grey Level threshold values to determine defects.

13. The method of claim 1, wherein the semiconductor wafer is manufactured according to one or more of technologies characterized by High Aspect Ratio (HAR), the one or more technologies comprising Via in Trench (VIT), Dynamic Random Access Memory (DRAM), or Vertical Negative-AND (VNAND).

14. A Critical Dimensions Scanning Electron Microscope (CD-SEM) comprising:
    a unit to obtain CD-SEM measurements of a semiconductor wafer;
    a Back Scattering Electron (BSE) imaging unit to obtain a Grey Level (GL) image of the semiconductor wafer;
    a unit to perform GL analysis of the GL image and to process the GL analysis results with reference to results of the CD-SEM measurements; and
    a unit to perform a defect analysis of the semiconductor wafer based on the GL analysis of the GL image and the CD-SEM measurements.

15. The CD-SEM according to claim 14, further comprising:
    a block to provide primary knowledge on a location of a feature on the semiconductor wafer.

16. The CD-SEM according to claim 14, further comprising:
 BSE detectors to collect BSE data for the BSE imaging unit.

17. The CD-SEM according to claim 14, wherein the unit to perform the GL analysis is further to perform Inverse Transformation of the GL image to restore original BSE data on physical signals.

18. The CD-SEM according to claim 17, wherein the unit to perform the GL analysis is to respectively perform measurements of Uniformity, Contrast, and Contours of a feature or group of features fabricated on the semiconductor wafer based on the restored original BSE data.

19. The CD-SEM according to claim 17, further comprising:
 a unit to detect material properties and defects of the semiconductor wafer based on one or more measurements of Uniformity, Contrast, and Contours of a feature or group of features.

20. A non-transitory computer readable storage medium comprising data that, when accessed by a processing device, cause the processing device to perform operations comprising:
 concurrently performing operations to obtain Critical Dimensions Scanning Electron Microscope (CD-SEM) measurements of a semiconductor wafer and an analysis of a Grey Level image of the semiconductor wafer by a material-sensitive and High Aspect Ratio (HAR) sensitive imaging technology; and
 processing together results of the CD-SEM measurements of the semiconductor wafer and the analysis of the Grey Level image of the wafer obtained by the material-sensitive and HAR-sensitive imaging technology.

* * * * *